(12) United States Patent
Barrett et al.

(10) Patent No.: US 8,027,823 B2
(45) Date of Patent: Sep. 27, 2011

(54) METHODS AND SYSTEM FOR VIEWING GENOMIC DATA

(75) Inventors: Michael T. Barrett, Mountain View, CA (US); Michael P. Caren, Palo Alto, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 1496 days.

(21) Appl. No.: 11/473,869

(22) Filed: Jun. 23, 2006

(65) Prior Publication Data

US 2007/0299616 A1 Dec. 27, 2007

(51) Int. Cl.
*G06G 7/58* (2006.01)
*G06F 7/60* (2006.01)
*G01N 33/48* (2006.01)
*C12Q 1/68* (2006.01)

(52) U.S. Cl. .................. 703/11; 702/19; 702/20; 703/2; 700/90; 435/6

(58) Field of Classification Search .................. None
See application file for complete search history.

(56) References Cited

U.S. PATENT DOCUMENTS

| | | |
|---|---|---|
| 2003/0220820 A1 | 11/2003 | Sears et al. |
| 2004/0061702 A1 | 4/2004 | Kincaid et al. |
| 2005/0076313 A1 | 4/2005 | Pegram et al. |
| 2005/0240358 A1 | 10/2005 | Sasaki et al. |
| 2008/0294613 A1 * | 11/2008 | Iyer et al. .......... 707/4 |

OTHER PUBLICATIONS

Knutsen et al., Genes, Chromosomes & Cancer, vol. 44, pp. 52-64, 2005.*
Knutsen et al., The SKY/CGH Database for Spectral Karyotyping and Comparative Genomic Hybridization Data, 2003, Nat. Cancer Inst. and Nat. Center for Biotech. Infor., 10-1 thru 10-14.
Speicher et al., The New Cytogenetics: Blurring the Boundaries with Molecular Biology, 2005, www.nature.com/review/genetics, 6: 782-792.
Trask, Barbara J., Human Cytogenetics: 46 Chromosomes, 46 Years and Counting, 2002, Genetics, Nature Reviews, 3: 769-778.

* cited by examiner

*Primary Examiner* — Shubo Zhou
(74) *Attorney, Agent, or Firm* — James S. Keddie; Shweta H. Chandra; Bret E. Field (57) ABSTRACT

A computer-implemented method for viewing experimental data is provided. In certain embodiments the method comprises: a) inputting genomic array data and cytogenetic data into a computer memory; and b) producing a graphical user interface comprising: i) a chromosomal map of the genomic array data comprising a first positional indicator that indicates a position on the chromosomal map; and ii) a cytogenetic map of the cytogenetic data comprising a second positional indicator that indicates a position on the cytogenetic map.

21 Claims, 3 Drawing Sheets
(1 of 3 Drawing Sheet(s) Filed in Color)

CGH Genomic
Locator Line
Dynamically Linked
to the Cytogenetic
Assay Locator Line

B)

Cytogenetic = Locator
Line Dynamically
Linked to the CGH
Locator Line

Cytogenetic map
shows 3 copies of chr
17 and single copy
17p deletion

METHODS AND SYSTEM FOR VIEWING GENOMIC DATA

BACKGROUND

Genomic instability leads to complex patterns of chromosomal rearrangements in certain cells, e.g., cancer cells. These events are associated with copy number changes as well as translocations and rearrangements affecting multiple chromosomes in a single cell. Array CGH (aCGH) is a widely used technology for investigating genomes of interest. However aCGH data is typically plotted across normal reference chromosomes and does not represent the in vivo structures of chromosomes in cancer cells. Thus structural lesions frequently seen in cancer cells, such as derivative and marker chromosomes, inversions and ring chromosomes cannot be identified in aCGH assays. In addition many of the translocations reported in cancer cells appear to be balanced at the level of resolution provided by the light or fluorescent microscope. Thus the absence of copy number change associated with these lesions obscures them from detection by CGH analyses. In addition to somatically acquired genomic changes recent investigations have identified naturally occurring copy number variants (CNVs) in the human genome that may mediate human variation and disease. These CNVs include duplications, inversions and deletions of variable sizes ranging from cytogenetic bands to individual genes. Although aCGH can measure the copy number variations associated with CNVs, in certain cases it cannot determine the orientation and relative positions of each copy of these variations in a genome.

Cytogenetics is typically used for identifying balanced translocations, marker chromosomes, and other genomic structures present in a sample of interest. Standard cytogenetic assays, such as Giemsa (G) banding have identified numerous cancer-specific translocations and chromosome abnormalities in cancer cells such as the Philadelphia (t9,22) chromosome. Improvements in cytogenetic banding and visualization such as M banding and spectral karyotyping (SKY) have enabled detailed analyses on a chromosome by chromosome basis of inversions and translocations, as well as the identification of regions of losses in cancers of interest. Furthermore these assays provide an assessment of chromosome copy number as well as structural integrity on a cell-by-cell basis in a sample of interest.

SUMMARY

A computer-implemented method for viewing experimental data is provided. In certain embodiments the method comprises: a) inputting genomic array data and cytogenetic data into a computer memory; and b) producing a graphical user interface comprising: i) a chromosomal map of the genomic array data comprising a first positional indicator that indicates a position on the chromosomal map; and ii) a cytogenetic map of the cytogenetic data comprising a second positional indicator that indicates a position on the cytogenetic map. In certain embodiments, the first and second positional indicators may be dynamically linked, such that movement of one of the positional indicators to a second position on one of the maps automatically results in movement of the other positional indicator to a corresponding position on other map.

BRIEF DESCRIPTION OF THE FIGURES

The patent or application file contains at least one drawing executed in color. Copies of this patent application publication with color drawing(s) will be provided by the U.S. Patent and Trademark Office upon request and payment of the necessary fee

DEFINITIONS

The terms "nucleic acid" and "polynucleotide" are used interchangeably herein to describe a polymer of any length, e.g., greater than about 10 bases, greater than about 100 bases, greater than about 500 bases, greater than 1000 bases, usually up to about 10,000 or more bases composed of nucleotides, e.g., deoxyribonucleotides or ribonucleotides, or compounds produced synthetically (e.g., PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions. Naturally-occurring nucleotides include guanine, cytosine, adenine and thymine (G, C, A and T, respectively).

The terms "ribonucleic acid" and "RNA" as used herein mean a polymer composed of ribonucleotides.

The terms "deoxyribonucleic acid" and "DNA" as used herein mean a polymer composed of deoxyribonucleotides.

The term "oligonucleotide" as used herein denotes a single stranded multimer of nucleotide of from about 10 to 200 nucleotides. Oligonucleotides are usually synthetic and, in many embodiments, are under 80 nucleotides in length. Oligonucleotides may contain ribonucleotide monomers (i.e., may be oligoribonucleotides) or deoxyribonucleotide monomers.

The term "oligomer" is used herein to indicate a chemical entity that contains a plurality of monomers. As used herein, the terms "oligomer" and "polymer" are used interchangeably, as it is generally, although not necessarily, smaller "polymers" that are prepared using the functionalized substrates of the invention, particularly in conjunction with combinatorial chemistry techniques. Examples of oligomers and polymers include polydeoxyribonucleotides (DNA), polyribonucleotides (RNA), other nucleic acids that are C-glycosides of a purine or pyrimidine base, polypeptides (proteins), polysaccharides (starches, or polysugars), and other chemical entities that contain repeating units of like chemical structure.

The term "sample" as used herein relates to a material or mixture of materials, typically, although not necessarily, in fluid form, containing one or more components of interest.

The terms "nucleoside" and "nucleotide" are intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the terms "nucleoside" and "nucleotide" include those moieties that contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like.

The phrase "surface-bound nucleic acid", e.g., a surface bound interfering RNA molecule, refers to a nucleic acid that is immobilized on a surface of a solid substrate, where the substrate can have a variety of configurations, e.g., a sheet, bead, or other structure. In certain embodiments, the nucleic acid probes employed herein are present on a surface of the same planar support, e.g., in the form of an array.

An "array," includes any two-dimensional or substantially two-dimensional (as well as a three-dimensional) arrangement of spatially addressable regions bearing nucleic acids, particularly oligonucleotides or synthetic mimetics thereof, and the like, e.g., RNAi oligonucleotides. Where the arrays are arrays of nucleic acids, the nucleic acids may be adsorbed, physisorbed, chemisorbed, or covalently attached to the arrays at any point or points along the nucleic acid chain.

Any given substrate may carry one, two, four or more arrays disposed on a surface of the substrate. Depending upon the use, any or all of the arrays may be the same or different from one another and each may contain multiple spots or features. An array may contain one or more, including more than two, more than ten, more than one hundred, more than one thousand, more ten thousand features, or even more than one hundred thousand features, in an area of less than 20 cm$^2$ or even less than 10 cm$^2$, e.g., less than about 5 cm$^2$, including less than about 1 cm$^2$, less than about 1 mm$^2$, e.g., 100 µm$^2$, or even smaller. For example, features may have widths (that is, diameter, for a round spot) in the range from a 10 µm to 1.0 cm. In other embodiments each feature may have a width in the range of 1.0 µm to 1.0 mm, usually 5.0 µm to 500 µm, and more usually 10 µm to 200 µm. Non-round features may have area ranges equivalent to that of circular features with the foregoing width (diameter) ranges. At least some, or all, of the features are of different compositions (for example, when any repeats of each feature composition are excluded the remaining features may account for at least 5%, 10%, 20%, 50%, 95%, 99% or 100% of the total number of features). Inter-feature areas will typically (but not essentially) be present which do not carry any nucleic acids (or other biopolymer or chemical moiety of a type of which the features are composed). Such inter-feature areas typically will be present where the arrays are formed by processes involving drop deposition of reagents but may not be present when, for example, photolithographic array fabrication processes are used. It will be appreciated though, that the inter-feature areas, when present, could be of various sizes and configurations.

Each array may cover an area of less than 200 cm$^2$, or even less than 50 cm$^2$, 5 cm$^2$, 1 cm$^2$, 0.5 cm$^2$, or 0.1 cm$^2$. In certain embodiments, the substrate carrying the one or more arrays will be shaped generally as a rectangular solid (although other shapes are possible), having a length of more than 4 mm and less than 150 mm, usually more than 4 mm and less than 80 mm, more usually less than 20 mm; a width of more than 4 mm and less than 150 mm, usually less than 80 mm and more usually less than 20 mm; and a thickness of more than 0.01 mm and less than 5.0 mm, usually more than 0.1 mm and less than 2 mm and more usually more than 0.2 mm and less than 1.5 mm, such as more than about 0.8 mm and less than about 1.2 mm.

Arrays can be fabricated using drop deposition from pulse-jets of either precursor units (such as nucleotide or amino acid monomers) in the case of in situ fabrication, or the previously obtained nucleic acid. Such methods are described in detail in, for example, the previously cited references including U.S. Pat. Nos. 6,242,266, 6,232,072, 6,180,351, 6,171,797, 6,323,043, U.S. patent application Ser. No. 09/302,898 filed Apr. 30, 1999 by Caren et al., and the references cited therein. As already mentioned, these references are incorporated herein by reference. Other drop deposition methods can be used for fabrication, as previously described herein. Also, instead of drop deposition methods, photolithographic array fabrication methods may be used. Inter-feature areas need not be present particularly when the arrays are made by photolithographic methods as described in those patents.

An array is "addressable" when it has multiple regions of different moieties (e.g., different oligonucleotide sequences) such that a region (i.e., a "feature" or "spot" of the array) at a particular predetermined location (i.e., an "address") on the array contains a particular sequence. Array features are typically, but need not be, separated by intervening spaces.

The term "mixture", as used herein, refers to a combination of elements, that are interspersed and not in any particular order. A mixture is heterogeneous and not spatially separable into its different constituents. Examples of mixtures of elements include a number of different elements that are dissolved in the same aqueous solution, or a number of different elements attached to a solid support at random or in no particular order in which the different elements are not spatially distinct. In other words, a mixture is not addressable. To be specific, an array of surface-bound oligonucleotides, as described below, is not a mixture of surface-bound oligonucleotides because the species of surface-bound oligonucleotides are spatially distinct and the array is addressable.

The terms "determining", "measuring", "evaluating", "assessing" and "assaying" are used interchangeably herein to refer to any form of measurement, and include determining if an element is present or not. These terms include both quantitative and/or qualitative determinations. Assessing may be relative or absolute. "Assessing the presence of" includes determining the amount of something present, as well as determining whether it is present or absent.

The term "using" has its conventional meaning, and, as such, means employing, e.g., putting into service, a method or composition to attain an end. For example, if a program is used to create a file, a program is executed to make a file, the file usually being the output of the program. In another example, if a computer file is used, it is usually accessed, read, and the information stored in the file employed to attain an end. Similarly if a unique identifier, e.g., a barcode is used, the unique identifier is usually read to identify, for example, an object or file associated with the unique identifier.

A "computer-implemented method" is a method that is executed using a computer. In certain cases, the computer may execute programming for performing the method.

A "graphical user interface" or "GUI" is a screen of a display, e.g., a computer monitor, that may be viewed by a user. A graphical user interface may contain at least one image, as well as a moveable cursor that is connected to a computer system.

The term "genomic array data" refers to data produced by an array-based genomic assay, e.g., an assay in which a sample containing labeled genomic DNA is hybridized with an array of nucleic acid probes. A comparative genome hybridization (CGH) assay is a type of array-based genomic assay.

Figure 1:
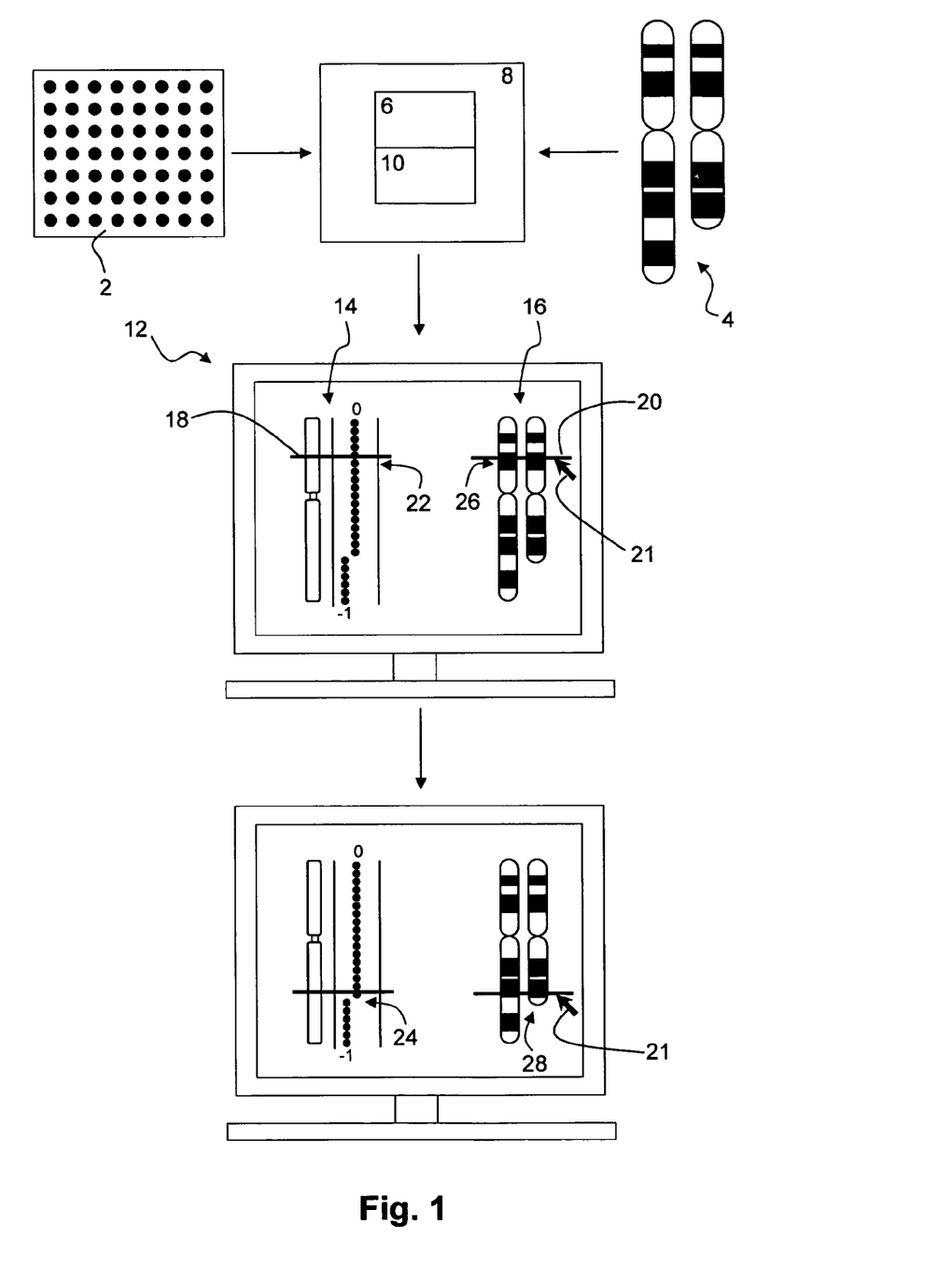
FIG. 1 illustrates a first embodiment of the subject methods.

As used herein, the term "chromosomal map" refers to a graphical representation in which data points obtained from an array-based genomic assay are arranged in order along a chromosome. The data points are arranged in order according to the chromosomal binding sites of the probes used to produce the data points. Exemplary chromosomal maps are shown in FIG. 1 and in FIG. 4d of Speicher et al. (Nature Reviews 2005 6: 782-792). A chromosomal map may show data for one or more chromosomes.

The term "cytogenetic data" refers to data for at least part of a stained chromosome. The data may show a banding pattern or a fluorescence pattern, for example. The data may be graphical or digital, for example.

The term "cytogenetic map" is a graphical representation of cytogenetic data, as shown on a graphical user interface. A "cytogenetic map" may be an image of at least part of a stained chromosome, for example. A cytogenetic map may show one or more chromosomes that may contain bands or may be color coded.

The term "positional indicator" is used to refer to a marker that identifies a position on a chromosomal map or cytogenetic map.

The term "dynamically linked", in reference to positional indicators that are dynamically linked, is used to refer to positional indicators that identify corresponding positions on a chromosomal map and cytogenetic map. When one of the positional indicators is moved to another position in a map, e.g., by "clicking and dragging" that positional indicator, the positional indicator in the other map moves to a corresponding position in that map.

The term "corresponding positions", with reference to corresponding positions on a chromosomal map and a cytogenetic map, is used to refer to the same position on the chromosomal map and the cytogenetic map. For example, the position corresponding to 17q24-17q25 in a chromosomal map is position 17q24-17q25 in the cytogenetic map. Corresponding positions are positionally equivalent to each other. In the case of derivative chromosomes, for example, equivalent positions on a chromosomal map and a cytogenetic map can be on different chromosomes, as long as those equivalent positions both provide information for the same region of DNA. For example, corresponding positions of a hybrid chromosome that contains the long arm of chromosome 1 and the short arm of chromosome 2 (as shown in a cytogenetic map), lie on chromosome 1 and chromosome 2 on the chromosomal map, respectively.

DESCRIPTION OF THE SPECIFIC EMBODIMENTS

A computer-implemented method for viewing experimental data is provided. In certain embodiments the method comprises: a) inputting genomic array data and cytogenetic data into a computer memory; and b) producing a graphical user interface comprising: i) a chromosomal map of the genomic array data comprising a first positional indicator that indicates a position on the chromosomal map; and ii) a cytogenetic map of the cytogenetic data, comprising a second positional indicator that indicates a position on the cytogenetic map. In certain embodiments, the first and second positional indicators may be dynamically linked, such that movement of one of the positional indicators to a second position on one of the maps automatically results in movement of the other positional indicator to a corresponding position on other map.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It must be noted that as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Computer-implemented Methods

As summarized above, a computer-implemented method for viewing genomic data is provided. One embodiment of the subject computer-implemented method may be described with reference to FIG. 1. With reference to FIG. 1, one embodiment of the method includes inputting genomic array data 2 (e.g., raw or processed data produced by an array-based comparative genome hybridization assay) and cytogenetic data 4 (e.g., an image of one, two, three or more stained chromosomes that show banding patterns or color codes) into memory 6 of computer 8. The genomic array data and the cytogenetic data are processed by processor 10 of computer 8 to produce an output that is displayed on a graphical user interface 12 (e.g., a computer monitor). The graphical user interface shows a chromosomal map 14 that schematically represents the genomic array data and a cytogenetic map 16 that schematically represents the cytogenetic data. The chromosomal map 14 and cytogenetic map 16 each have a positional indicator, i.e., positional indicators 18 and 20, respectively, that indicate a chromosomal position on both the chromosomal map 14 and the cytogenetic map 16. In general terms, positional indicators 18 and 20 indicate the corresponding position on the chromosomal map 14 and the cytogenetic map 16, where a corresponding position on the two maps identifies the same chromosomal region on each of the maps. The positional indicators may indicate, for example, the same chromosome arm on the chromosomal map 14 and the cytogenetic map 16, or an equivalent sub-region of the same chromosome arm on each of the maps. As noted above, in certain embodiments, the two positional indicators (i.e., the first and second positional indicators) are dynamically linked in that movement of one of the positional indicators from one position to another causes movement of the other positional indicator to a corresponding, i.e., positionally equivalent, position on the other map. As illustrated in FIG. 1, movement of positional indicator 18 from position 22 of chromosomal map 14 to position 24 (e.g., using cursor 21) causes the automatic movement of positional indicator 20 from position 26 of the cytogenetic map (wherein position 26 in the cytogenetic map corresponds to position 22 of the chromosomal map) to position 28 (where position 28 of the chromosomal map corresponds to position 24 of the chromosomal map).

In other words, the first and second positional indicators are dynamically linked in that movement of one of the positional indicators follows the movement of the other positional indicator. The dynamic linkage of the positional indicators provides a graphical user interface in which corresponding positions of a chromosomal map (i.e., a graphical representation of the results from an array-based genomic hybridization assay) and a cytogenetic map are indicated. A user may move either of the positional indicators (either the positional indicator of the chromosomal map or the positional indicator of the cytogenetic map) from one location to another in one map, and the positional indicator of the other map moves to a corresponding location, either at the same time as or immediately after, the first positional indicator is moved.

The dynamically-linked movement of the two positional indicators enables a user to readily look at the same chromosomal locations in both maps. In use of the subject system, a user may readily correlate copy number changes indicated by the chromosomal map (e.g., an increase or decrease in copy number of a particular chromosomal segment) with structural changes indicated in the cytogenetic map. For example and with reference to FIG. 1, a user may identify a region in a chromosomal map that indicates an altered copy number (e.g., position 24). By moving the positional indicator of the chromosomal map to that region, the positional indicator of the cytogenetic map moves to the equivalent region in the cytogenetic map and user can readily observe the structural change that produced the altered copy number. In the example shown in FIG. 1, the chromosomal map indicates that one copy of the lower half of a chromosome is deleted, and that the deletion point is at position 28. Movement of a positional indicator to that position in the chromosomal map causes movement of the positional indicator of the cytogenetic map to move to the corresponding position, allowing the user to readily see that the alteration in copy number (as shown in by the chromosomal map) is due to a deletion a distal part of the long arm of a chromosome.

Depending on the type of data being analyzed and the interests of the user, the dynamically-linked positional indicators may be moved between two different positions of a single chromosome arm, two different positions of the same chromosome or two different positions on different chromosomes, for example. As noted above, certain chromosomes, e.g., derivative or marker chromosomes, are hybrids of one or more chromosomes. Examples of such chromosomes are shown in panel B FIG. 2, and schematically illustrated in FIG. 3. In certain embodiments, the corresponding positions of two different regions of a single hybrid chromosome on the cytogenetic map may be on two different chromosomes on the chromosomal map. Illustrated by example, the cytogenetic map 30 shows a chromosome that has the short arm of chromosome 1 and the long arm of chromosome 2. When the positional indicator is located on the short arm of that chromosome, the short arm of chromosome 1 is indicated by the other positional indicator of the chromosomal map 32. Movement of the positional indicator to the long arm of the chromosome on the cytogenetic map causes movement of the positional indicator of the chromosomal map to the long arm of chromosome 2. Further, once a region of interest is identified, the method may also provide for simultaneously zooming in (i.e., enlarging) and out (i.e., reducing the size) of the same region of interest in both of the maps, thus allowing a region of interest to be investigated at various levels of detail.

Input of genomic array data and cytogenetic data may be done by selecting or uploading pre-existing data sets that may be stored locally or at a remote location. In certain embodiments, the results of an array-based genomic hybridization assay and the results of a cytogenetic assay may be forwarded to the user prior to the input of those results into the computer memory. The two sets of data are usually obtained from the same cell type. In other words, the same cell type may be examined using cytological methods and using an array-based genomic hybridization method to provide data that is input into computer memory. In one embodiment, a single sample may be split and assayed using the two different methods.

The genomic array data may be raw data or processed data obtained from an array-based genomic hybridization assay. In certain embodiments, the genomic array data may be processed data that contains an evaluation (e.g., a floating point number such as a ratio or the like) of the copy number of each probe of a set of probes. The genomic locations of those probes may be known, allowing a chromosomal map graphically representing the input genomic array data to be produced. Data for at least one region a chromosome, e.g., a region of at least 100 kb to 1 Mb in length, a chromosome arm, a chromosome, a subset of the chromosomes of a cell or the entire chromosome content of cell (including sex chromosomes and/or autosomes) may be input into the computer memory.

Methods for producing and analyzing array-based genomic hybridization assay data are reviewed in Speicher et al. (Nature Reviews (2005) 6: 782-792), Ylstra et al. (Nucleic Acids Res. (2006) 34:445-50), Vissers et al. (Hum. Mol. Genet. (2005) 14 R215-23) and Pinkel (Ann. Rev. Genomics Hum. Genet. (2005) 6:331-54) and described in great detail in Pinkel et al. (Nat. Genet. (1998) 20:207-211), Hodgson et al. (Nat. Genet. (2001) 29:459-464) and Wilhelm et al. (Cancer Res. (2002) 62: 957-960), as well as many others. Such methods may be employed herein.

Similar to the genomic array data, the cytogenetic data may include data for at least one region a chromosome, e.g., a region of at least 100 kb to 1 Mb in length, a chromosome arm, a chromosome, a subset of the chromosomes of a cell or the entire chromosome content of cell (including sex chromosomes and/or autosomes). In one embodiment, a karyotype, i.e., an image of entire complement of chromosomes of a cell may be employed. A cytogenetic map (particularly if karyotypic data is employed) may show homologous chromosomes (e.g., a chromosome pair or, in certain embodiments, three, four or five chromosomes) aligned next to each other. As would be readily apparent, the positional indicator may, in certain embodiments, indicate equivalent positions in all of the homologous chromosomes.

Cytogenetic data may be produced by any convenient method. Chromosomes may be stained (i.e., labeled to show banding patterns or chromosome identity) using, for example, Giemsa, quinacrine, a fluorochrome, or a FISH-based method. G-banding and M-banding are examples of staining systems that show chromosomal bands. In one embodiment, the staining method employed is a multicolor FISH-based method that allows the visualization of all 24 autosomes, each in a different color. Such "chromosome painting" approaches are reviewed in Speicher et al. (Nature Reviews (2005) 6: 782-792), Liehr et al (Histol. Histopathol. (2004) 19:229-37) and Matthew et al (Methods Mol. Biol. (2003) 220: 213-33) and include multiplex-FISH (M-FISH; Speicher et al, Nature Genet. (1996) 12: 368-375), spectral karyotyping (SKY; Schrock et al, Science (1996) 273: 494-497) and combined binary ratio labeling (COBRA; Tanke et al, Eur. J. Hum. Genet. (1999) 7: 2-11). Such methods provide for identification of intrachromosomal rearrangements, and may be performed on genomic samples from non-dividing or metaphase cells for example.

As would be apparent, the position indicators may be of any type or shape. For example, the positional indicator may be a cursor such as a line, arrow, circle or square, for example. A positional indicator may be moved by a user by inputting instructions for moving the positional indicator into a computer. For example, instructions may be input into a computer using a keyboard connected to the computer implementing the above-described method, e.g., using the arrow buttons on or keyboard, or a computer mouse, for example. In one embodiment, one positional indicator may be moved by moving a cursor onto the positional indicator using a computer mouse and depressing a button on the mouse, and then moving the mouse, i.e., by "clicking and dragging".

The subject method includes executing computer-readable instructions that are at a remote location to the user, and transmitting data from the remote location to the graphical user interface at the user's location. In certain embodiments, the genomic array data and cytogenetic data may be received from a remote location, and the programming executed locally to the user.

The above-described computer-implemented method may be executed using programming that may be written in one or more of any number of computer programming languages. Such languages include, for example, Java (Sun Microsystems, Inc., Santa Clara, Calif.), Visual Basic (Microsoft Corp., Redmond, Wash.), and C++ (AT&T Corp., Bedminster, N.J.), as well as any many others.

Appropriate operating systems for use in conjunction with the programming include, but are not limited to, Solaris (Sun Microsystems, Inc., Santa Clara, Calif.), Windows (Microsoft Corp., Redmond, Wash.), Mac (Apple Computer, Inc., Cupertino, Calif.), or Linux (Red Hat, Inc., Raleigh, N.C.). Appropriate software applications include, but are not limited to, relational databases such as Oracle 9.0.1 (9i) (Oracle Corp., Redwood Shores, Calif.), DB2 Universal Database V8.1 (IBM Corp., Armonk, N.Y.), PostgreSQL (PostgreSQL, Inc., Wolfville, NS Canada), or SQL Server 2000 (Microsoft Corp., Redmond, Wash.).

As noted above, one embodiment involves two tiers of infrastructure: a server tier and a client tier. In one embodiment, the server tier may be an workgroup server (Sun Microsystems, Inc., Santa Clara, Calif.), the operating system may be Solaris (Sun Microsystems, Inc., Santa Clara, Calif.), and the database software may be Oracle 9.0.1 (9i) (Oracle Corp., Redwood Shores, Calif.). In the same embodiment, the client tier may operate using the Windows operating system (Microsoft Corp., Redmond, Wash.). In this embodiment, a Java language-based application, running on the client may contain both business and presentation logic. A Java Runtime Engine (JRE) may interpret and execute the compiled application within the client operating system (e.g. Windows). In addition to proprietary presentation and business logic, the client application may rely on third party application programming interfaces (APIs) for common functionality such as application connectivity and database connectivity. Installing APIs and a database on a server may provide a scalable solution for information sharing and propagating updates among numerous client applications. Each client may communicate with a server-based APIs through the local area network using common protocols (e.g. TCP/IP) supported by both the client and server operating systems (e.g. Windows and Solaris).

Computer Readable Media

In certain embodiments, the above-described methods are coded onto a computer-readable medium in the form of programming, where the term "computer readable medium" as used herein refers to any storage or transmission medium that participates in providing instructions and/or data to a computer for execution and/or processing. Examples of storage media include floppy disks, magnetic tape, CD-ROM, a hard disk drive, a ROM or integrated circuit, a magneto-optical disk, or a computer readable card such as a PCMCIA card and the like, whether or not such devices are internal or external to the computer. A file containing information may be "stored" on computer readable medium, where "storing" means recording information such that it is accessible and retrievable at a later date by a computer.

In certain embodiments, a computer-readable medium comprising instructions for producing a graphical user interface comprising: i) a chromosomal map of genomic array data comprising a first positional indicator that indicates a position on the chromosomal map; and ii) a cytogenetic map comprising a second positional indicator that indicates a position on the cytogenetic map; wherein the first and second positional indicators are dynamically linked, is provided.

With respect to computer readable media, "permanent memory" refers to memory that is permanent. Permanent memory is not erased by termination of the electrical supply to a computer or processor. Computer hard-drive ROM (i.e. ROM not used as virtual memory), CD-ROM, floppy disk and DVD are all examples of permanent memory. Random Access Memory (RAM) is an example of non-permanent memory. A file in permanent memory may be editable and re-writable.

A computer-based system comprising the above-referenced computer readable medium is also provided. The minimum hardware of the computer-based systems of the present invention comprises a central processing unit (CPU), input means, output means, and data storage means. A skilled artisan can readily appreciate that any one of the currently available computer-based system are suitable for use in the present invention. The data storage means may comprise any manufacture comprising a recording of the present information as described above, or a memory access means that can access such a manufacture.

To "record" data, programming or other information on a computer readable medium refers to a process for storing information, using any such methods as known in the art. Any convenient data storage structure may be chosen, based on the means used to access the stored information. A variety of data processor programs and formats can be used for storage, e.g. word processing text file, database format, etc.

A "processor" references any hardware and/or software combination that will perform the functions required of it. For example, any processor herein may be a programmable digital microprocessor such as available in the form of a electronic controller, mainframe, server or personal computer (desktop or portable). Where the processor is programmable, suitable programming can be communicated from a remote location to the processor, or previously saved in a computer program product (such as a portable or fixed computer readable storage medium, whether magnetic, optical or solid state device based). For example, a magnetic medium or optical disk may carry the programming, and can be read by a suitable reader communicating with each processor at its corresponding station.

One or more platforms present in the subject systems may be any type of known computer platform or a type to be developed in the future, although they typically will be of a class of computer commonly referred to as servers. However, they may also be a main-frame computer, a work station, or other computer type. They may be connected via any known or future type of cabling or other communication system including wireless systems, either networked or otherwise. They may be co-located or they may be physically separated. Various operating systems may be employed on any of the computer platforms, possibly depending on the type and/or make of computer platform chosen. Appropriate operating systems include Windows NT®, Sun Solaris, Linux, OS/400, Compaq Tru64 Unix, SGI IRIX, Siemens Reliant Unix, and others.

In certain embodiments, the subject devices include multiple computer platforms which may provide for certain benefits, e.g., lower costs of deployment, database switching, or changes to enterprise applications, and/or more effective firewalls. Other configurations, however, are possible. For example, as is well known to those of ordinary skill in the relevant art, so-called two-tier or N-tier architectures are possible rather than the three-tier server-side component architecture represented by, for example, E. Roman, Mastering Enterprise JavaBeans™ and the Java™2 Platform (John Wiley & Sons, Inc., NY, 1999) and J. Schneider and R. Arora, Using Enterprise Java. (Que Corporation, Indianapolis, 1997).

It will be understood that many hardware and associated software or firmware components that may be implemented in a server-side architecture for Internet commerce are known and need not be reviewed in detail here. Components to implement one or more firewalls to protect data and applications, uninterruptable power supplies, LAN switches, web-server routing software, and many other components are not shown. Similarly, a variety of computer components customarily included in server-class computing platforms, as well as other types of computers, will be understood to be included but are not shown. These components include, for example, processors, memory units, input/output devices, buses, and other components noted above with respect to a user computer. Those of ordinary skill in the art will readily appreciate how these and other conventional components may be implemented.

The functional elements of system may also be implemented in accordance with a variety of software facilitators and platforms (although it is not precluded that some or all of the functions of system may also be implemented in hardware or firmware). Among the various commercial products available for implementing e-commerce web portals are BEA WebLogic from BEA Systems, which is a so-called "middleware" application. This and other middleware applications are sometimes referred to as "application servers," but are not to be confused with application server hardware elements. The function of these middleware applications generally is to assist other software components (such as software for performing various functional elements) to share resources and coordinate activities.

Other development products, such as the Java™2 platform from Sun Microsystems, Inc. may be employed in the system to provide suites of applications programming interfaces (API's) that, among other things, enhance the implementation of scalable and secure components. Various other software development approaches or architectures may be used to implement the functional elements of system and their interconnection, as will be appreciated by those of ordinary skill in the art.

Additional system components, methods, arrays and kits may be include as are described in U.S. patent application Ser. No. 11/001,700, filed Nov. 30, 2004, U.S. patent application Ser. No. 11/001,672, filed Nov. 30, 2004 and U.S. patent application Ser. No. 11/000,681, filed Nov. 30, 2004, the entireties of which are incorporated by reference herein.

Kits

Kits for use in connection with the subject invention may also be provided. Such kits may include at least a computer readable medium including programming as discussed above and instructions. The instructions may include installation or setup directions. The instructions may include directions for use of the invention with options or combinations of options as described above. In certain embodiments, the instructions include both types of information.

Providing the software and instructions as a kit may serve a number of purposes. The combination may be packaged and purchased as a means of upgrading array analysis software. Alternately, the combination may be provided in connection with new software. In certain embodiments, the instructions will serve as a reference manual (or a part thereof) and the computer readable medium as a backup copy to the preloaded utility.

The instructions may be recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging), etc. In other embodiments, the instructions are present as an electronic storage data file present on a suitable computer readable storage medium, e.g., CD-ROM, diskette, etc, including the same medium on which the program is presented.

In yet other embodiments, the instructions are not themselves present in the kit, but means for obtaining the instructions from a remote source, e.g. via the Internet, are provided. An example of this embodiment is a kit that includes a web address where the instructions can be viewed and/or from which the instructions can be downloaded. Conversely, means may be provided for obtaining the subject programming from a remote source, such as by providing a web address. Still further, the kit may be one in which both the instructions and software are obtained or downloaded from a remote source, as in the Internet or world wide web. Some form of access security or identification protocol may be used to limit access to those entitled to use the subject invention. As with the instructions, the means for obtaining the instructions and/or programming is generally recorded on a suitable recording medium.

In addition to the subject feature programming, the kits may also include one or more reference sets of data, e.g., two or more sets of array data and cytogenetic data for use in testing the software after software installation.

Utility

The nuclear genome of the cells of a cellular sample may be evaluated using the above-described method. In one embodiment, the method may be employed for the quantitative comparison of copy number of one nucleic acid sequence in a first collection of nucleic acid molecules relative to the copy number of the same sequence in a second collection.

Arrays employed in CGH assays contain polynucleotides immobilized on a solid support. Array platforms for performing the array-based methods are generally well known in the art (e.g., see Pinkel et al., Nat. Genet. (1998) 20:207-211;

Hodgson et al., Nat. Genet. (2001) 29:459-464; Wilhelm et al., Cancer Res. (2002) 62: 957-960) and, as such, need not be described herein in any great detail. In general, CGH arrays contain a plurality (i.e., at least about 100, at least about 500, at least about 1000, at least about 2000, at least about 5000, at least about 10,000, at least about 20,000, usually up to about 100,000 or more) of addressable features that are linked to a planar solid support. Features on a subject array usually contain a polynucleotide that hybridizes with, i.e., binds to, genomic sequences from a cell. Accordingly, such "comparative genome hybridization arrays", for short "CGH arrays" typically have a plurality of different BACs, cDNAs, oligonucleotides, or inserts from phage or plasmids, etc., that are addressably arrayed. As such, CGH arrays usually contain surface bound polynucleotides that are about 10-200 bases in length, about 201-5000 bases in length, about 5001-50,000 bases in length, or about 50,001-200,000 bases in length, depending on the platform used.

In particular embodiments, CGH arrays containing surface-bound oligonucleotides, i.e., oligonucleotides of 10 to 100 nucleotides and up to 200 nucleotides in length, find particular use in the subject methods.

In general, the subject assays involve labeling a test and a reference genomic sample to make two labeled populations of nucleic acids which may be distinguishably labeled, contacting the labeled populations of nucleic acids with an array of surface bound polynucleotides under specific hybridization conditions, and analyzing any data obtained from hybridization of the nucleic acids to the surface bound polynucleotides. Such methods are generally well known in the art (see, e.g., Pinkel et al., Nat. Genet. (1998) 20:207-211; Hodgson et al., Nat. Genet. (2001) 29:459-464; Wilhelm et al., Cancer Res. (2002) 62: 957-960)) and, as such, need not be described herein in any great detail.

Two different genomic samples may be differentially labeled, where the different genomic samples may include an "experimental" sample, i.e., a sample of interest, and a "control" sample to which the experimental sample may be compared. In certain embodiments, the different samples are pairs of cell types or fractions thereof, one cell type being a cell type of interest, e.g., an abnormal cell, and the other a control, e.g., a normal cell. If two fractions of cells are compared, the fractions are usually the same fraction from each of the two cells. In certain embodiments, however, two fractions of the same cell type may be compared. Exemplary cell type pairs include, for example, cells isolated from a tissue biopsy (e.g., from a tissue having a disease such as colon, breast, prostate, lung, skin cancer, or infected with a pathogen etc.) and normal cells from the same tissue, usually from the same patient; cells grown in tissue culture that are immortal (e.g., cells with a proliferative mutation or an immortalizing transgene), infected with a pathogen, or treated (e.g., with environmental or chemical agents such as peptides, hormones, altered temperature, growth condition, physical stress, cellular transformation, etc.), and a normal cell (e.g., a cell that is otherwise identical to the experimental cell except that it is not immortal, infected, or treated, etc.); a cell isolated from a mammal with a cancer, a disease, a geriatric mammal, or a mammal exposed to a condition, and a cell from a mammal of the same species, preferably from the same family, that is healthy or young; and differentiated cells and non-differentiated cells from the same mammal (e.g., one cell being the progenitor of the other in a mammal, for example). In one embodiment, cells of different types, e.g., neuronal and non-neuronal cells, or cells of different status (e.g., before and after a stimulus on the cells, or in different phases of the cell cycle) may be employed. In another embodiment of the invention, the experimental material is cells susceptible to infection by a pathogen such as a virus, e.g., human immunodeficiency virus (HIV), etc., and the control material is cells resistant to infection by the pathogen. In another embodiment of the invention, the sample pair is represented by undifferentiated cells, e.g., stem cells, and differentiated cells.

Results obtained such an array-based CGH assay may be compared to results obtained from a cytogenetic assay using the methods described above.

EXAMPLES

The following examples are put forth so as to provide those of ordinary skill in the art with a complete disclosure and description of how to make and use the present invention, and are not intended to limit the scope of what the inventors regard as their invention. Efforts have been made to ensure accuracy with respect to numbers used (e.g. amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

Figure 2:
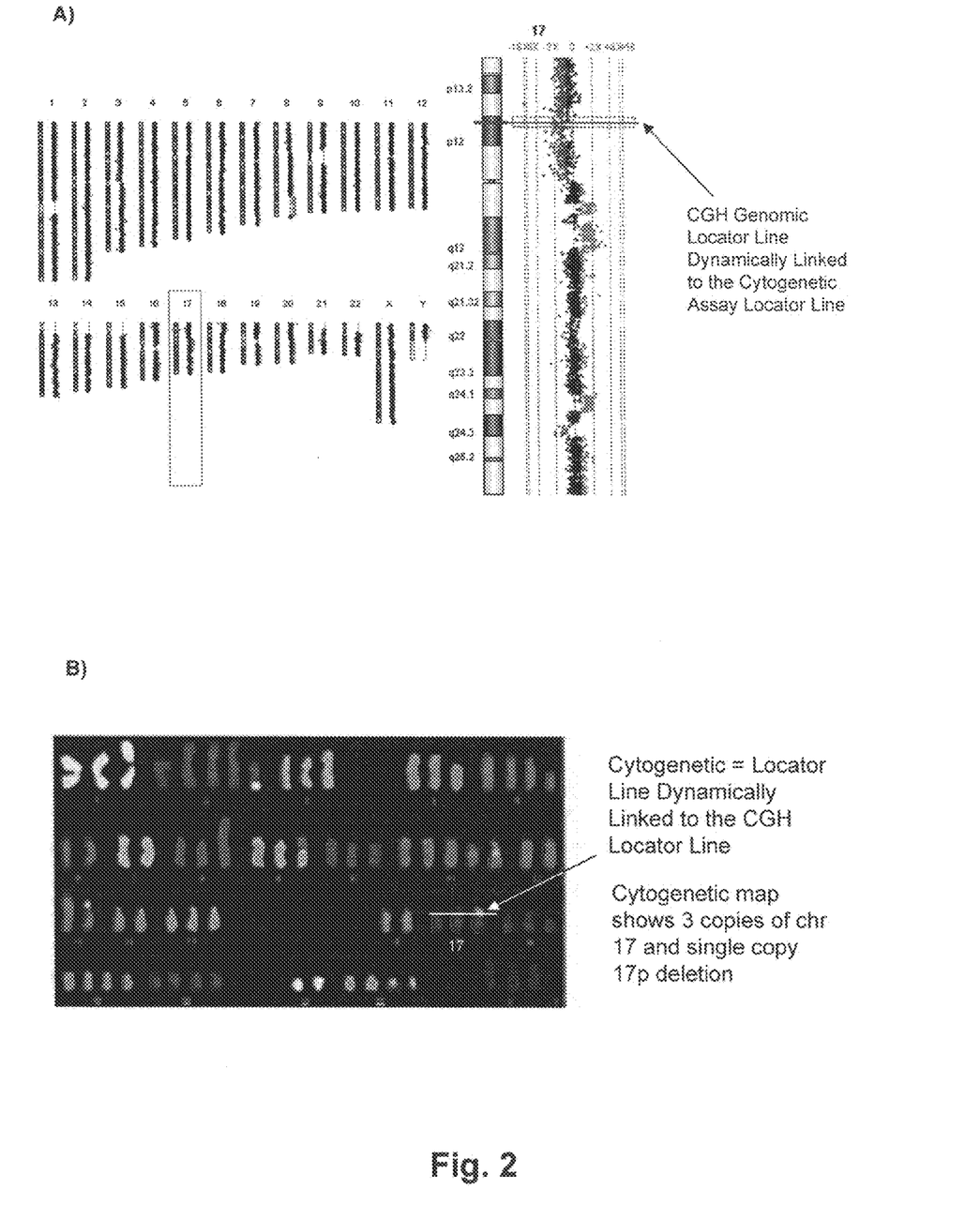
FIG. 2 illustrates a second embodiment of the subject methods.
Figure 3:
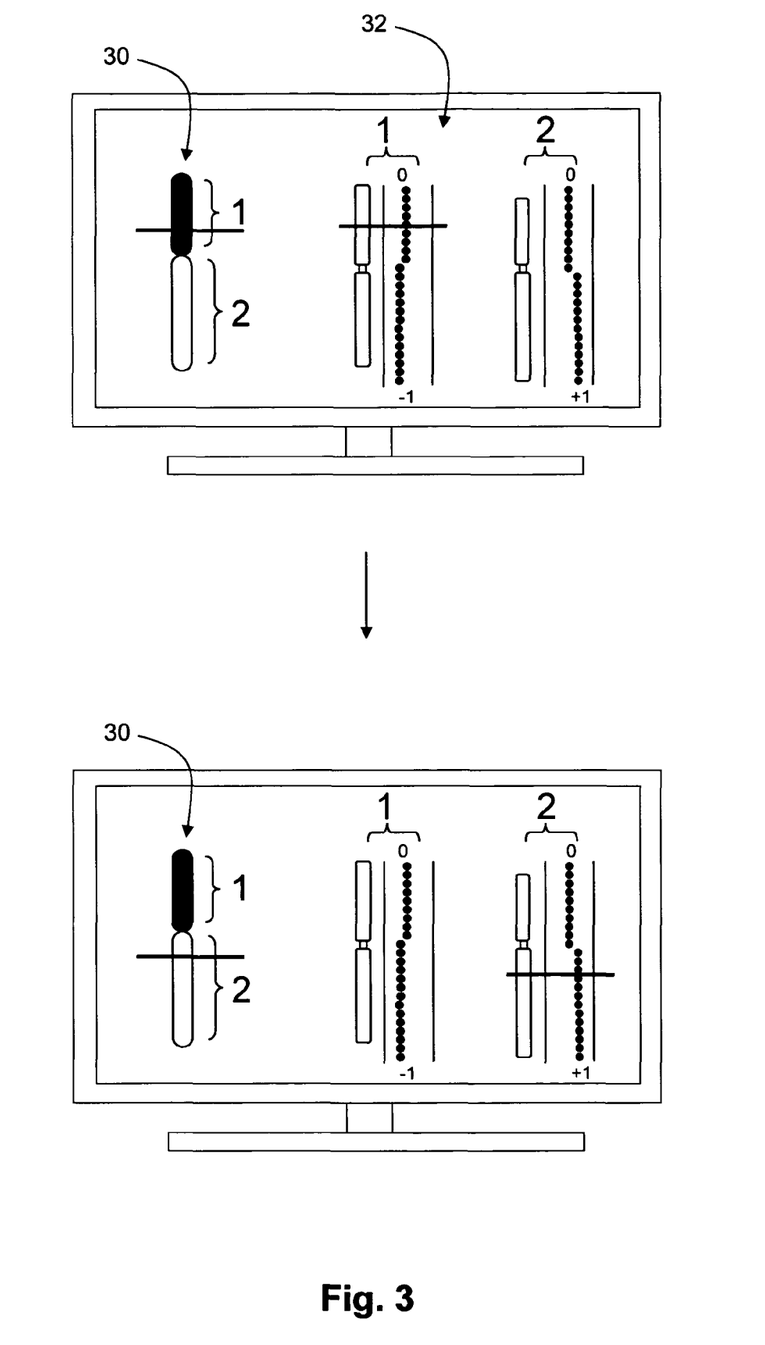
FIG. 3 illustrates a third embodiment of the subject methods.

With reference to FIG. 2, the positional indicator line of the SKY assay of panel B is linked to the positional indicator line in CGH results of panel A. In this case the precise location of the deletion on chromosome 17p and the amplification on chromosome 17q selected in CGH Analytics is simultaneously shown in the cytogenetics assay. This allows the user to view and interpret both types of data sets in a comprehensive and detailed manner. For example aCGH data (panel A) shows a loss of 17p in the colon carcinoma cell line HT-29. The SKY data (panel B) reveals the presence of 3 copies of chromosome 17 with truncation of the p arm in one copy. Thus with this interface the user can quickly determine that the loss of 17p in this cell line involves the entire p arm of chromosome 17 and affects one of three copies of the chromosome. In addition the same data integration can help resolve amplification events such as a small amplicon on 17q detected by aCGH.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A computer-implemented method for viewing experimental data, comprising:
   a) inputting genomic array data and cytogenetic data into a computer memory; and
   b) producing a graphical user interface comprising:
      i) a chromosomal map of said genomic array data comprising a first positional indicator that indicates a position on said chromosomal map; and ii) a cytogenetic map of said cytogenetic data comprising a second positional indicator that indicates a position on said cytogenetic map;

wherein said first and second positional indicators are dynamically linked.

2. The computer-implemented method of claim 1, wherein said first and second positional indicators identify corresponding positions on said chromosomal map and said cytogenetic map, respectively.

3. The method of claim 1, wherein movement of said first positional indicator to a second position on said chromosomal map results in movement of said second positional indicator to a corresponding position on said cytogenetic map.

4. The method of claim 1, wherein movement of said second positional indicator to a second position on said cytogenetic map results in movement of said first positional indicator to a corresponding position on said chromosomal map.

5. The method of claim 1, wherein said genomic array data is comparative genome hybridization data.

6. The method of claim 1, wherein said cytogenetic map is a color image of a fluorescently-labeled chromosome.

7. The method of claim 1, wherein said first and second positional indicators are arrows.

8. The method of claim 1, wherein said first and second positional indicators are lines.

9. The method of claim 1, further comprising inputting instructions to move at least one of said first and second positional indicators to a second position on said chromosomal map or said cytogenetic map, respectively.

10. The method of claim 9, wherein said inputting includes moving a cursor on said graphical user interface.

11. The method of claim 1, wherein said inputting comprises selecting or entering.

12. The method of claim 1, wherein said method further includes executing computer-readable instructions that are at a remote location and transmitting data from said remote location to said graphical user interface.

13. The method of claim 1, wherein said method further includes receiving said genomic array data and cytogenetic data from a remote location.

14. A non-transient computer-readable storage medium comprising computer programming instructions for performing the steps of the method of claim 1.

15. A computer comprising the computer readable medium of claim 14.

16. The computer of claim 15, further comprising a user interface for inputting genomic array data and cytogenetic data into a computer memory.

17. A method comprising:
  a) performing an array-based genomic hybridization assay and a cytogenetic assay on a cellular sample to produce genomic array data and cytogenetic data;
  b) inputting said genomic array data and said cytogenetic data into a computer of claim 15; and
  c) executing said instructions to produce a graphical user interface comprising:
    i) a chromosomal map of said genomic array data comprising a first positional indicator that indicates a position on said chromosomal map; and
    ii) a cytogenetic map of said cytogenetic data comprising a second positional indicator that indicates a position on said cytogenetic map;
  wherein said first and second positional indicators are dynamically linked.

18. The method of claim 17, wherein said array-based genomic hybridization assay is an array-based comparative genome hybridization assay.

19. The method of claim 17, wherein said cytogenetic assay is a FISH assay.

20. The method of claim 17, further including analyzing said chromosomal map and said cytogenetic map to identify an alteration in a chromosome.

21. The method of claim 17, further comprising moving said first or second positional indicators.

* * * * *